(12) United States Patent
Itabashi et al.

(10) Patent No.: US 7,362,438 B2
(45) Date of Patent: Apr. 22, 2008

(54) COD MEASURING METHOD AND DEVICE

(75) Inventors: Toshihisa Itabashi, Kyoto (JP); Yozo Morita, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 36 days.

(21) Appl. No.: 11/204,999

(22) Filed: Aug. 17, 2005

(65) Prior Publication Data

US 2006/0097182 A1 May 11, 2006

(30) Foreign Application Priority Data

Nov. 5, 2004 (JP) ............................. 2004-321429

(51) Int. Cl.
*G01N 21/00* (2006.01)
(52) U.S. Cl. ...................................... 356/432
(58) Field of Classification Search ................ 356/432, 356/436
See application file for complete search history.

(56) References Cited

U.S. PATENT DOCUMENTS

| | | | | |
|---|---|---|---|---|
| 4,790,654 A | * | 12/1988 | Clarke | ......................... 356/310 |
| 5,420,432 A | * | 5/1995 | Manook et al. | .............. 250/373 |
| 5,641,966 A | | 6/1997 | Karlberg et al. | |
| 5,842,150 A | | 11/1998 | Renberg et al. | |
| 5,864,140 A | | 1/1999 | Owens et al. | |
| 6,643,016 B2 | * | 11/2003 | Garver et al. | ................ 356/320 |
| 6,816,257 B2 | * | 11/2004 | Goix | ........................... 356/318 |

OTHER PUBLICATIONS

European Search Report dated May 4, 2006.

* cited by examiner

*Primary Examiner*—Tarifur Chowdhury
*Assistant Examiner*—Isiaka O Akanbi
(74) *Attorney, Agent, or Firm*—Cheng Law Group PLLC

(57) ABSTRACT

A COD conversion equation holding unit in a computing unit of a COD measuring device holds a COD conversion equation that indicates a relationship between total-absorbance that is linearly combined by multiplying an absorbance value at each of a plurality of wavelengths by a weighting factor and a COD value, and a conversion unit finds a converted COD value by using the COD conversion equation, and outputs the resulting value. Preferably, a COD conversion equation calculation unit calculates a COD conversion equation based upon the relationship between the total absorbent and an actual measured COD value in sample water, and a correlation calculation unit finds a correlation with respect to each of a plurality of COD conversion equations calculated by the COD conversion equation calculation unit. In this case, the COD conversion equation holding unit holds the conversion equation having the best correlation among the COD conversion equations calculated by the COD conversion equation calculation unit as a COD conversion equation for the sample water.

26 Claims, 6 Drawing Sheets

(A)

(B)

(C)

CALCULATION OF CONVERTED COD VALUE

COD MEASURING METHOD AND DEVICE

BACKGROUND OF THE INVENTION

1. Field of the Invention

The present invention relates to a COD (chemical oxygen demand) measuring method which forms a COD conversion equation (regression equation) used for converting a ultraviolet-ray (UV) value to a COD value on the basis of the correlation between UV absorbance and a COD measured value in drainage, environmental water and the like, and based upon this conversion equation, provides a converted COD value from a UV value measured in sample water, and also concerns a device for such a method.

Here, COD is treated as a factor that includes BOD (biological oxygen demand).

2. Description of the Related Art

The Japanese Industrial Standard (JIS) has stipulated the ultraviolet photometer for monitoring of water pollution for use in water-quality monitoring, and the UV measured value is used in correlation with the COD value for calculating a water pollution loading amount and the like in connection with the total pollutant load control (see JIS K0807).

Upon measuring COD, an absorption photometer as shown in FIG. 6 is used. Light emitted from a light source 1 such as a low-pressure mercury lamp is directed to a measuring cell 2. The measuring cell 2 sends a sample to a space having a predetermined optical path length, and the light from the light source 1 is transmitted through the space. The light transmitted through the measuring cell 2 is allowed to transmit an interference filter 3 so that a specific wavelength, for example, 254 nm, is selected and detected by a detector 4, and the detection signal is converted to an absorbance value by an amplifier 5.

The COD component is mainly composed of organic substances, and most of the substances absorb ultraviolet rays; thus, by utilizing this characteristic, the correlation between the absorbance of a specific wavelength (normally 254 nm) in the ultraviolet region and a COD measured value obtained in a separate manner is examined to prepare a COD conversion equation so that the absorbance is converted to the corresponding COD value.

Moreover, a method has been proposed in which, by utilizing the fact that underwater turbidity mostly relates to visible light region, the absorbance of visible light (normally 546 nm) is measured simultaneously with the absorbance of ultraviolet rays so that influences from turbidity in sample water are removed by using the differential absorbance between the ultraviolet-ray absorbance and visible light absorbance.

With respect to the COD conversion equation, the following linear regression equation is used:

$$Y = a + bX$$

(Y: converted COD value, X: UV absorbance value or differential absorbance value, a: intercept, b: gradient)

However, as shown in FIGS. 7 to 9, with respect to the organic compound and inorganic compound, the absorption spectrum in the ultraviolet region varies greatly depending on the substances. In the case of the normally-used 254 nm also, some exert a great absorbance value while others exert a small absorbance value, and some of them hardly exert any absorbance (see Table 1).

TABLE 1

(Concentration 100 mg/L, Cell Length 10 mm)

| Name of compound | Absorbance | Name of compound | Absorbance |
|---|---|---|---|
| Phenol | 0.463 | Hippuric acid | 1.235 |
| p-Cresol | 0.396 | Albumin (bovine serum) | 0.025 |
| Phenyl acetate | 0.161 | Lignin (alkali) | 3.492 |
| Benzoic acid | 0.595 | Methanol | 0.000 |
| Cinnamic acid | 9.134 | Glucose | 0.000 |
| Salicyclic acid | 0.671 | L-Glutamic acid | 0.000 |
| Fumaric acid | 0.808 | Cellulose | 0.011 |
| Aniline | 0.771 | Acetic acid | 0.000 |

(Extracted from JIS K 0807 Description)

Normally, various substances are contained in sample water, and the composition of substances varies depending on the sample water. For this reason, the COD conversion equation, obtained by using absorbance in a single ultraviolet-ray wavelength, tends to fail to provide a desirable correlation to COD.

SUMMARY OF THE INVENTION

The objective of the present invention is to apply an appropriate COD conversion equation to sample water in a suitable manner so as to provide a converted COD value that hardly has a relative error to an actual COD value.

As clearly indicated by absorption spectra of various substances shown in FIGS. 7 to 9, some substances exert absorbance in other wavelengths even if the absorbance thereof in 254 nm is small. Based upon this fact, the present invention simultaneously measures the absorbance in each of a plurality of wavelengths, such as 225 nm, 275 nm and 300 nm, in addition to 254 nm (the number being generally indicated by m). Of course with the wavelength at which the absorbance is measured not being limited to these, other wavelengths may be used as long as the substance relating to COD measurements (regardless of whether it is an organic substance or an inorganic substance) exerts absorption thereon. For example, by using a wavelength in the vicinity of 240 nm, detection of nitrite ions ($NO_2^-$) that form COD components is available.

Moreover, the absorbance to be measured is not limited to absorbance from a single wavelength and includes an absorbance integral value within a predetermined range of wavelength.

In the COD measuring method of the present invention, a plurality of wavelengths are set as wavelengths on which the COD component measuring absorbance is measured in sample water within an ultraviolet region, and with respect to the COD conversion equation, the absorbance in each of the plurality of wavelengths is subjected to a weighting process to obtain a linearly combined function so that the resulting equation obtained from the function, which indicates the correlation between the total-absorbance and the COD value, is used.

That is, the present COD measuring method comprises the steps of selecting a plurality of wavelengths for measuring COD components in a sample water within a ultraviolet region; preparing a COD conversion equation that indicates a relationship between absorbances of the sample water at the wavelengths and a COD value thereof, the COD conversion equation being a function which indicates a relationship between a total-absorbance and the COD value, the total-absorbance being a linearly combined function of the absorbances by a weighting process; measuring the absorbances of the sample water in the wavelengths; and calculating the COD value from the COD conversion equation by using the absorbances measured.

In this case, the absorbances include an absorbance integral value within a predetermined range of wavelength.

More specifically, x in the following equation (2), which is obtained by multiplying the absorbance at each of the wavelengths by a weighting factor so as to be linearly combined, is referred to as the total-absorbance. In equation (2), the total-absorbance is prepared as a value that is turbidity-corrected by subtracting the absorbance (Vis) at a wavelength in a visible region used for measuring turbidity correction, that is, the absorbance at 546 nm. Such a turbidity correction is preferably carried out; however, the turbidity correction is not necessarily required, and the application of the total-absorbance that is not turbidity-corrected is included within the scope of the present invention.

With respect to the COD conversion equation indicating the relationship between the total-absorbance x and the COD value, for example, the following equation (1) is used. However, not limited to this, the COD conversion equation may be another linear equation or quadratic equation.

$$y = a + bx \quad (1)$$

$$x = c1 \cdot Ab1 + c2 \cdot Ab2 + \ldots + cm \cdot Abm - Vis \quad (2)$$

in the equation, Ab1 to Abm: absorbance at each of wavelengths c1 to cm: weighting factor to absorbance at each of wavelength within an ultraviolet region The COD conversion equation is determined in the following manner.

With respect to the weighting factors of c1 to cm, several combinations are preliminarily prepared, and inputted to the device. With respect to the sets of weighting factors c1 to cm to be preliminarily prepared, the correlation between the COD value and measured wavelength in each of waste waters has been analyzed and found. With respect to sample water to be measured, the absorbances at a plurality of wavelengths and COD values are measured at a plurality of periods of time. A plurality of the COD conversion equations, which indicate relationships between respective total-absorbance values obtained by subjecting the absorbance for the COD components to respective weighting processes and the measured COD values, are prepared. Among the plurality of COD conversion equations, determining the equation that exhibits the best correlation as the COD conversion equation for the sample water.

For the determination on the superiority or inferiority of the correlation, for example, correlation coefficients, or relative errors between the converted COD values and the measured COD values, may be used, or both of the correlation coefficients and the relative errors may be used.

The COD measuring device of the present invention is provided with a light source that emits light within an ultraviolet region, a measuring cell that transmits light from the light source through sample water, a detector that receives and detects light that has been transmitted through the measuring cell, and a computing unit that calculates a converted COD value of the sample water from absorbance derived from the detection signals from the detector. The light source emits light including a plurality of wavelengths within the ultraviolet range. The detector detects light at a plurality of wavelengths within the ultraviolet region. The computing unit is provided with a COD conversion equation holding unit that holds a COD conversion equation that indicates the relationship between a total-absorbance that is a linear combination of the absorbances at the wavelengths multiplied by weighting factors and a COD value, and a conversion unit that applies the absorbances to the COD conversion equation held in the COD conversion equation holding unit to calculate the converted COD value and outputs the obtained value. Preferably, the total-absorbance in the COD conversion equation includes an absorbance derived from a wavelength in a visible region for measuring turbidity correction, in addition to the absorbance for measuring the COD components.

Preferably, the computing unit is further provided with a COD conversion equation calculation unit that calculates COD conversion equations based upon the relationship between the total-absorbance derived from absorbance values detected by the detector at a plurality of wavelengths and measured COD values on the sample water, calculating the COD conversion equations on a plurality set of weighting factors, and a correlation calculation unit that calculates a correlation with respect to each of the COD conversion equations calculated by the COD conversion equation calculation unit. In this case, the COD conversion equation holding unit holds the conversion equation having the best correlation found by the correlation calculation unit among the COD conversion equations calculated by the COD conversion equation calculation unit, as the COD conversion equation for the sample water. Here, the correlation, found by the correlation calculation unit, is one of the correlation coefficients and the relative error or both of these.

In the COD measuring method and device of the present invention, an equation indicating the relationship between the total-absorbance and COD value is used as the COD conversion equation; therefore, different from the conventional COD conversion equation in which absorbance for a single wavelength in the ultraviolet region is used, the best suited COD conversion equation can be used depending on the kinds of organic substances contained in the sample water, and it becomes possible to obtain a converted COD value that hardly has relative error to the actual COD value.

In the case of industrial wastes, the initial correlation tends to vary due to a change in materials, amount of manufactured products and the like. When the correlation is changed, the COD conversion equation no longer becomes best suited, failing to provide a COD conversion value with high precision (high reliability). Therefore, a plurality of combinations of weighting factors are prepared, and among the plurality of COD conversion equations found with respect to the sample water to be measured, the equation having the best correlation is used as the COD conversion equation for the sample water; thus, it becomes possible to properly cope with such a change in sample water and water samples of various kinds.

BRIEF DESCRIPTIONS OF DRAWINGS

Figure 4:
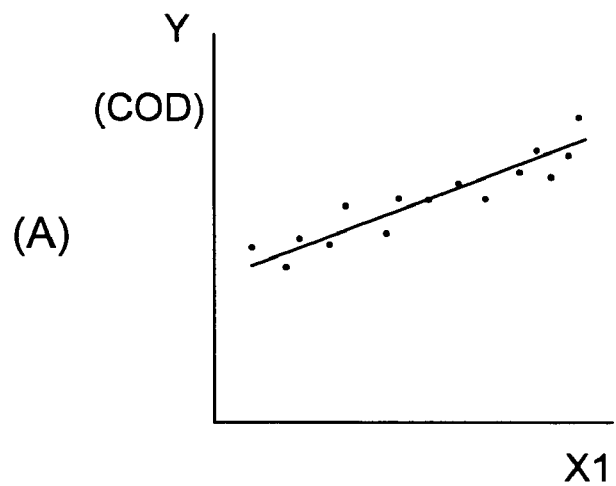
Figure 4:
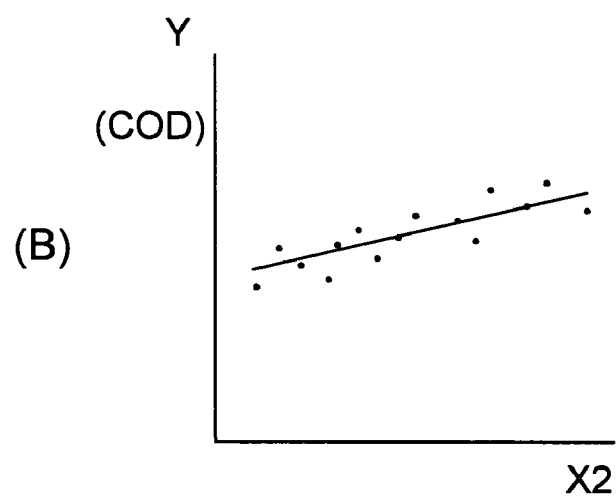
Figure 4:
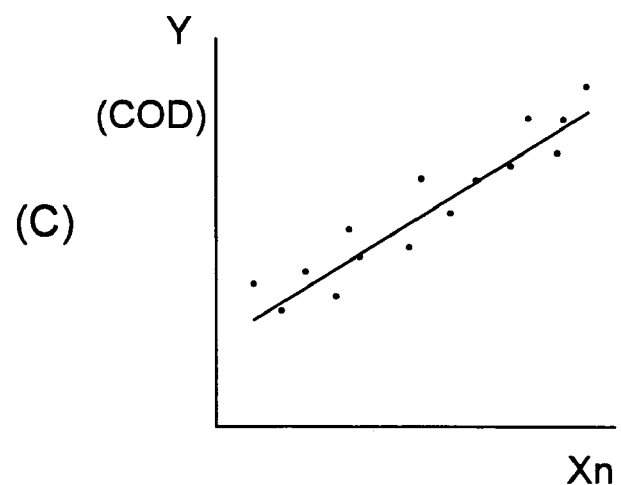

FIG. 4, consisting of FIGS. 4(a) to 4(c), is a drawing that indicates a correlation of each set of weighting factors in the embodiment.

Figure 5:
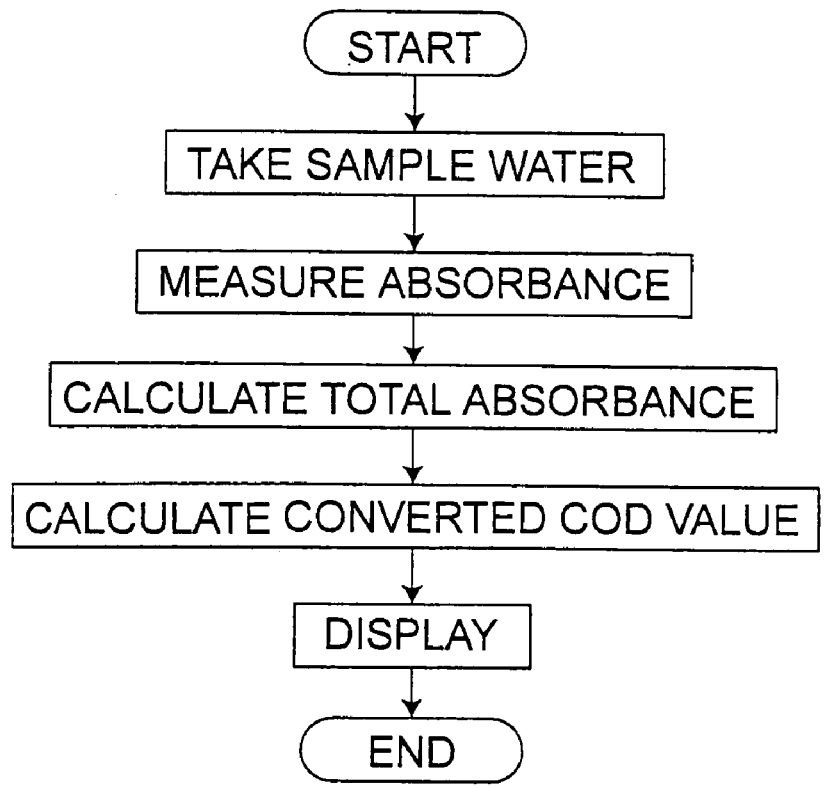

FIG. 5 is a flow chart that shows a sequence of processes used for calculating a converted COD value in the embodiment.

Figure 6:
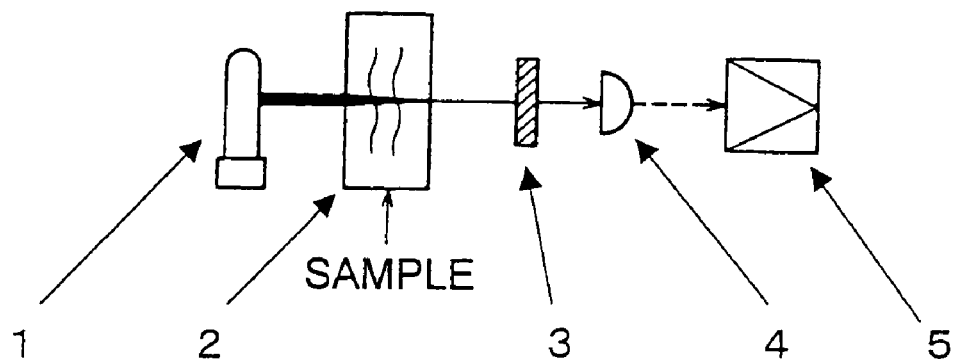

FIG. 6 is a schematic block diagram that shows one example of a conventional absorption photometer that can be used as a COD measuring device.

Figure 7:
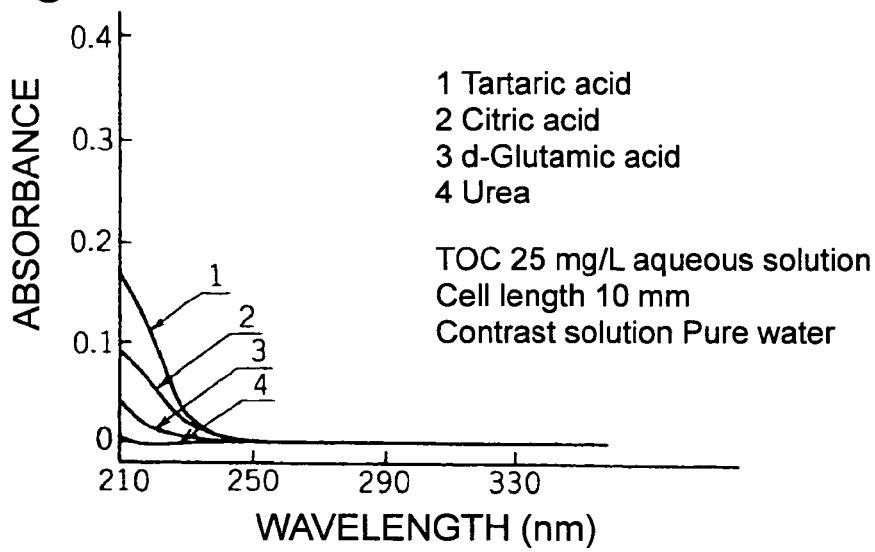

FIG. 7 is a graph that shows spectra of some organic compounds.

Figure 8:
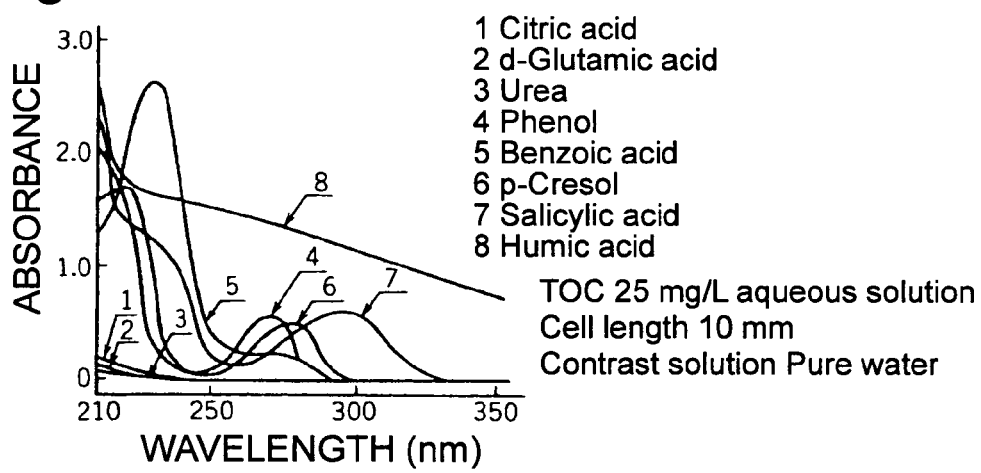

FIG. 8 is a graph that shows spectra of some organic compounds.

Figure 9:
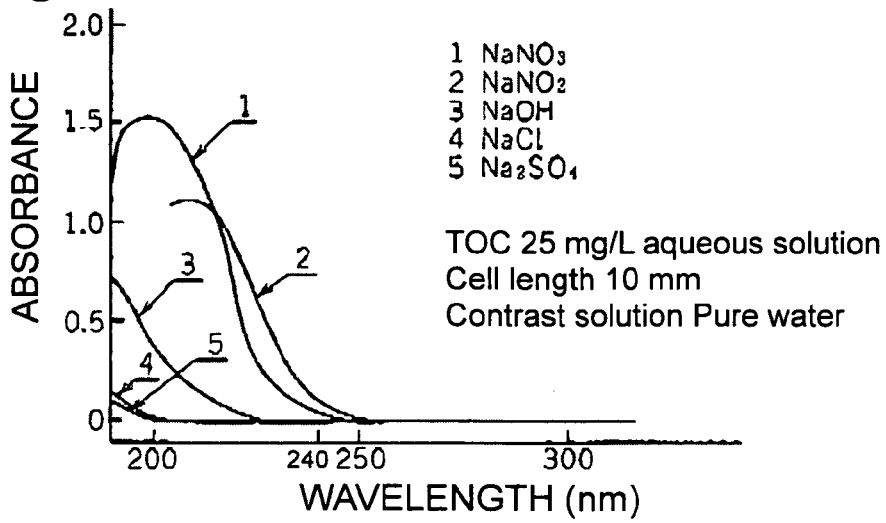

FIG. 9 is a graph that shows spectra of some inorganic compounds.

DESCRIPTION OF THE PREFERRED EMBODIMENTS

Figure 1:
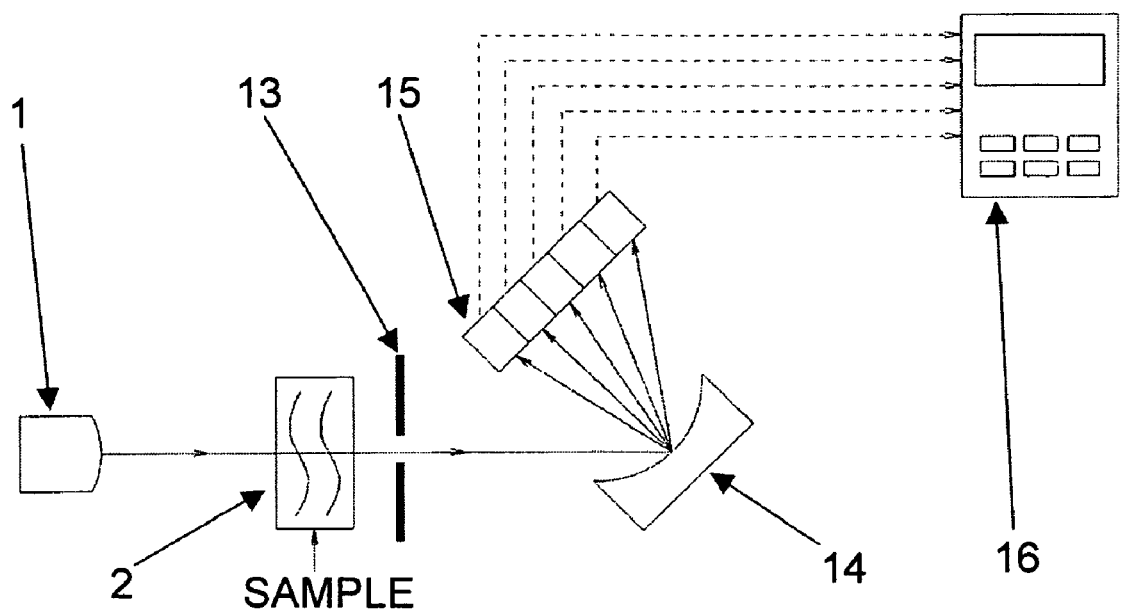
FIG. 1 is a schematic block diagram that shows one embodiment of an absorption photometer that can be used as a COD measuring device.

FIG. 1 is a schematic block diagram that shows one embodiment of an absorption photometer that can be used as a COD measuring device.

A light source that can emit continuous spectra covering an ultraviolet region and a visible region is preferably used as a light source 1. For example, a xenon lamp may be used. However, not limited to the xenon lamp, a mercury lamp that emits a plurality of luminescent line spectra covering the ultraviolet region and visible region may also be used as a light source. In the present embodiment, a light source such as a xenon lamp, which emits continuous spectra, is used.

A measuring cell 2 is a flow cell, and sample water is allowed to flow through it. The measuring cell 2 is made of synthetic quartz in its window member or in its entire cell so as to transmit light from the light source 1 through the sample water.

Reference numeral 14 indicates a grating that forms a spectrometer used for separating light having continuous spectra, and is prepared as, for example, a concave grating. An aperture 13, which forms an inlet slit of the spectrometer, is placed between the measuring cell 2 and the grating 14. A photodiode array 15 is placed at a position to receive light formed into spectra through the grating, and the photodiode array 15 is arranged so as to detect respective intensities of a plurality of wavelengths (for example, 225 nm, 254 nm, 275 nm, 300 nm and 546 nm). The grating 14 and the photodiode array 15 constitute a detector.

Reference numeral 16 indicates a computing/controlling device, and the computing/controlling device 16 is provided with an electric circuit that reads respective wavelength intensities from the photodiode array 15, a computing unit that carries out computing processes, such as conversion from the resulting wavelength intensities to COD values, an input device through which numeric values, measuring conditions and the like are inputted into the computing unit, a display device for displaying a measured converted COD value, and a control unit that carries out controlling operations on various parts inside the COD measuring device.

Figure 2:
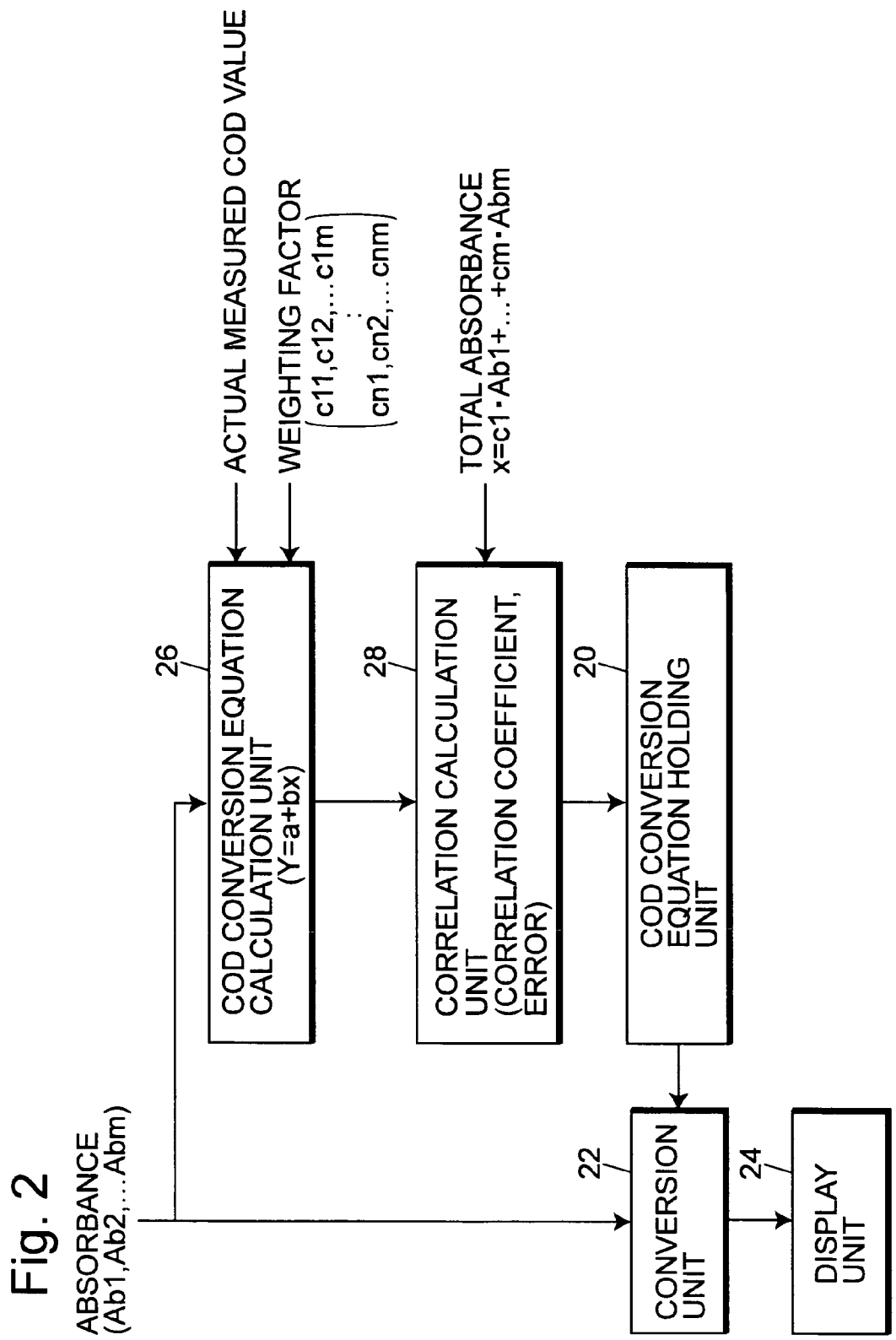
FIG. 2 is a block diagram that shows functions of a computing unit that is contained in a computing/controlling device in the embodiment.

FIG. 2 shows functions of a computing unit included in the computing/controlling device 16.

Reference numeral 20 indicates a COD conversion equation holding unit which holds a COD conversion equation (equation (1)) that indicates the relationship between the total-absorbance x derived from equation (2) which is linearly combined by multiplying absorbance values (Ab1, Ab2, . . . Abm) obtained based upon detection values at a plurality of wavelengths detected by the detector by respective weighting factors (c1, c2, . . . cm) and the COD value. The conversion unit 22 applies the respective absorbance values (Ab1, Ab2, . . . Abm) obtained based upon detection values at the plurality of wavelengths detected by the detector to the COD conversion equation held in the COD conversion equation holding unit 20 to find converted COD values, and outputs the resulting values.

In order to allow the COD conversion equation holding unit 20 to hold the COD conversion equation best suited for the sample water, the computing unit is further provided with a COD conversion equation calculation unit 26 that calculates a COD conversion equation from the relationship between the total-absorbance from the respective absorbance values (Ab1, Ab2, . . . Abm) obtained based upon detection values at the plurality of wavelengths detected by the detector and actual measured COD values with respect to the sample water, and carries out the calculating process of the COD conversion equation on each of a plurality of sets of weighting factors, and a correlation calculating unit 28 that finds the respective correlations with respect to a plurality of COD conversion equations calculated by the COD conversion equation calculating unit 26. The COD conversion equation holding unit 20 holds the best suited COD conversion equation found by the correlation calculating unit among the COD conversion equations calculated by the COD conversion equation calculating unit 26, as the COD conversion equation for the sample water.

Reference numeral 24 is a display unit which displays the converted COD value found by the conversion unit 22 and the correlation coefficient and relative errors found by the correlation calculating unit 28.

Figure 3:
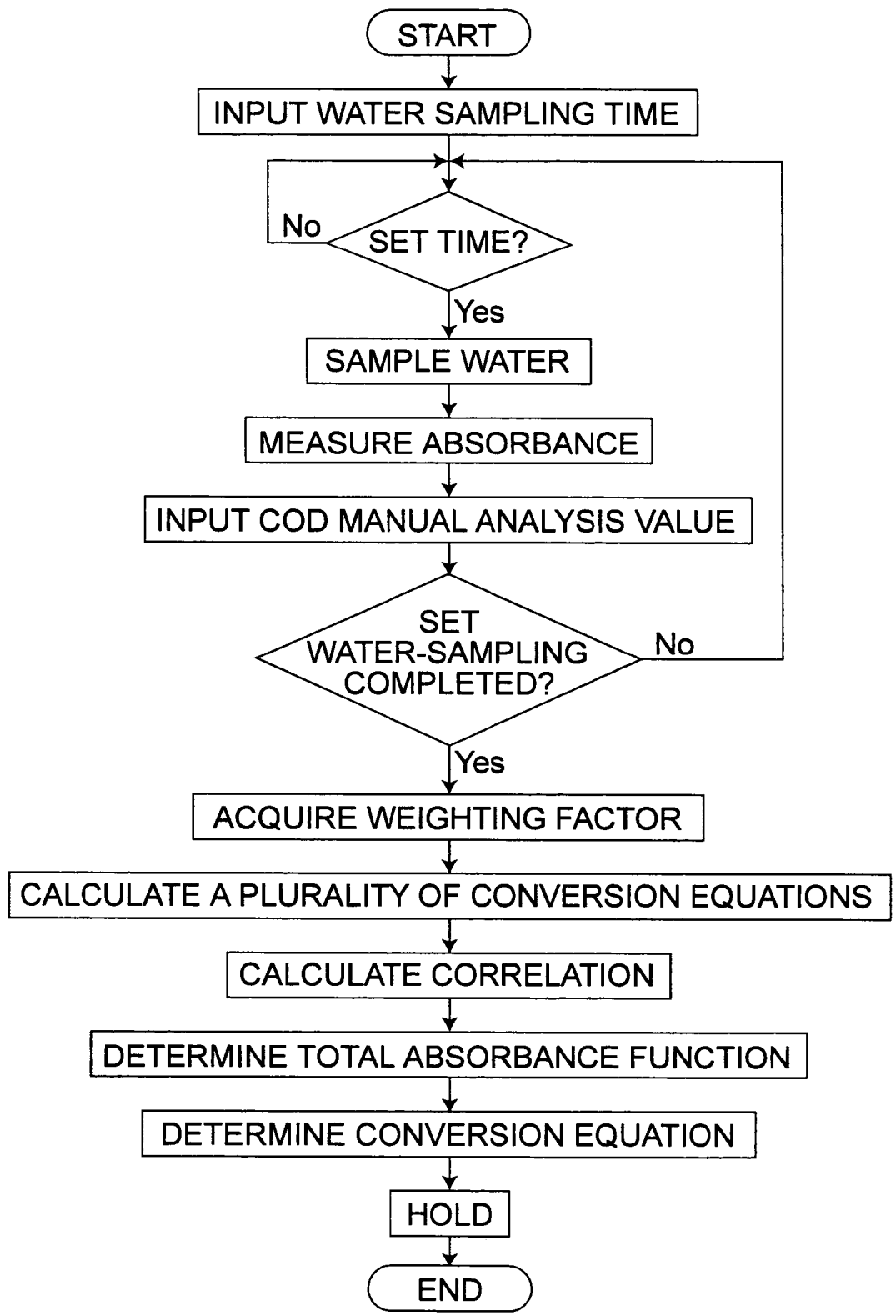
FIG. 3 is a flow chart that shows a sequence of processes used for determining a COD conversion equation in the embodiment.

Referring to FIG. 3, the following description will discuss a sequence of processes for determining the COD conversion equation.

A plurality of water sampling time are inputted and set. Upon arrival of the first set time, the COD measuring device starts sampling water. Then, the water is measured at predetermined wavelengths, and absorbance values at the respective wavelengths are found. With respect to the measured wavelengths, m-number of them within the ultraviolet region used for COD measurements and one of them in the visible region used for measuring turbidity correction are selected. At another end, the operator finds a COD value of the sample water through manual analyses, and inputs the resulting value. For example, as defined in JIS K0102, the COD manual analysis values are measured as the amount of consumption of potassium permanganate at 100° C., the amount of consumption of potassium permanganate at 20° C. and the amount of consumption of alkali potassium permanganate or the amount of consumption of potassium dichromate.

Until the set water-sampling time has been completed, the absorbance measurements and the COD manual analysis inputs are repeated during each of the set water-sampling time.

Upon completion of the absorbance measurements and the COD manual analysis inputs during the set water-sampling period of time, sets of weighting factors (c11, c12, . . . c1m), (c21, c22, . . . c2m) . . . (cn1, cn2, . . . cnm), which have been preliminarily inputted and set, are incorporated. By using these weighting factors, as indicated by the following equation (3), n-number of total-absorbance values (x1(t), x2(t), . . . xn(t)) are obtained for each of the water-sampling time (t).

$$x1(t)=c11 \cdot Ab1(t)+c12 \cdot Ab2(t)+ \ldots +c1m \cdot Abm(t)-\text{Vis}$$

$$x2(t)=c21 \cdot Ab1(t)+c22 \cdot Ab2(t)+ \ldots +c2m \cdot Abm(t)-\text{Vis}$$

$$\ldots$$

$$xn(t)=cn1 \cdot Ab1(t)+cn2 \cdot Ab2(t)+ \ldots +cnm \cdot Abm(t)-\text{Vis}$$

Ab1(t) to Abm(t) represent absorbance values at respective wavelengths within an ultraviolet region for COD measurements with respect to each of water-sampling time (t), and Vis is an absorbance value in a visible region for measuring turbidity correction.

Relationships between the COD manual analysis value at each of water-sampling times and the total-absorbance value (x1, x2, ... xn) using sets of respective weighting factors for the respective times are shown in FIGS. 4(A) to 4(C). These graphs thus obtained correspond to the number n of sets of the weighting factors. For the respective relationships, a regression straight line is found by, for example, a least square method. The regression straight line is indicated as a linear equation shown below:

$$y=a+bx \qquad (4)$$

The number of these regression equations corresponds to the number n of sets of the weighting factors. The regression equations are respectively placed in the respective graphs in FIGS. 4(A) to 4(C) as straight lines.

Next, with respect to each of the sets of weighting factors, the correlation is found. One example of the correlation is given as a correlation coefficient. The correlation coefficient r is defined as the following equation (5):

$$r = \frac{\sum (y_i - \bar{y})(x_i - \bar{x})}{\sqrt{\sum (y_i - \bar{y})^2 \cdot \sum (x_i - \bar{x})^2}} \qquad (5)$$

Here, yi represents a COD manual analyzed value at a certain water-sampling time, y bar (y with a bar attached thereon) represents an average value of COD manual analysis values, xi represents the total-absorbance at the water-sampling time, x bar (x with a bar attached thereon) represents the average value of the total-absorbance values. The square correlation coefficient $r^2$ may be used in place of the correlation coefficient r.

With respect to the correlation, not limited to the correlation coefficient, a relative error may be used. With respect to the relative error, when x is x bar, a difference (A) between a predetermined reliability limit value of y, for example, 95% reliability limit value, and y bar on the regression equation is divided by y bar so that the resulting value may be given as the relative error (for example see "Business handbook of the total pollutant load control", pages 153 to 162, written by Takao Saito, published by Kabushikigaisha Kankyoukougaishinbunsha, on Feb. 20, 1981).

The greatest one of the correlation coefficients thus obtained, or the smallest one of the relative errors, or the one which best satisfies both of these conditions is selected. This selection may be carried out automatically by the COD measuring device, or the correlation coefficient or the relative error is displayed so as to allow the user to manually select. Either the automatic selection or the manual selection may be made selectable through settings in the COD measuring device.

Here, supposing that the total-absorbance function derived from the set of weighting factors corresponding to the greatest one of the correlation coefficients or the smallest one of the relative errors is xj, the COD conversion equation using xj is indicated by the following equation:

$$y=a+bxj$$

Thus, this is the best suited COD conversion equation for the sample water. The conversion equation is held in the COD conversion equation holding unit 20.

These processes for finding the best suited COD conversion equation are preferably carried out at the time when the sample water is changed or when a predetermined period of time has elapsed; thus, the COD conversion equation to be used is preferably updated so as to become the best suited one.

Referring to FIG. 5, the following description will discuss the sequence of processes for calculating the converted COD value of actual sample water by using the COD conversion equation thus determined.

Upon starting measurements, the COD measuring device takes sample water, and the absorbance thereof is measured at each of a plurality of set wavelengths. These absorbance values are applied to the total-absorbance in the COD conversion equation so that the total-absorbance value is found, and the resulting total-absorbance value is used so that a converted COD value is calculated through the COD conversion equation. The resulting value is displayed.

In the above-mentioned embodiment, the weighting factors of the respective wavelengths are preliminarily inputted and set; however, a desired factor may be inputted through the input device of the main device.

Moreover, the weighting factors may be prepared as variable factors, and numeric values that indicate the correlation, that is, the correlation coefficient, the relative error and the like, at that time are calculated, and the one that provides the best suited correlation may be used among these. In this case, for example, each of the factors of the sets of weighting factors (c11, c12, ... c1m), (c21, c22, ... c2m) ... (cn1, cn2, ... cnm), as shown in the embodiment, is changed one by one.

For example, (1) each factor is changed from 0.1 to 1 by a scale of 0.1, and (2) with respect to each of factors from c11 to cnm, correlations are found with respect to all the combinations, and the best suited one is adopted.

Furthermore, although the COD conversion equation corresponds to linear approximation, high-order approximation (quadratic or higher approximation) may be used so as to provide a COD conversion equation having less relative error. For example, in the case of quadratic approximation, the approximate expression is indicated by:

$$y=a+bx+cx^2.$$

The change in approximation order may be made by altering the settings through programs in the COD measuring device.

The present invention can be utilized as a COD measuring device, such as an on-line UV meter, that finds a COD value by measuring ultraviolet-ray absorbance in drainage, environmental water or the like.

What is claimed is:

1. A COD measuring method comprising the steps of:
emitting spectra of light from a light source;
transmitting said light through sample water contained within a measuring cell;
detecting an absorbance of said light transmitted through said sample water, said absorbance being detected at wavelengths within said spectra; and
calculating a total-absorbance for said sample water, said total-absorbance being a total of weighted absorbances, wherein each of said weighted absorbances is said absorbance at one of said wavelengths within an ultraviolet range multiplied by a weighting factor from a set of said weighting factors, and wherein said absorbance for said wavelengths within an ultraviolet region of said spectra is uniquely associated with a weighting factor from a set of said weighting factors.

2. The COD measuring method according to claim 1, wherein said total is a sum total of weighted absorbances minus said absorbance at wavelengths within a visible region of said spectra.

3. The COD measuring method according to claim 1, wherein, prior to the step of calculating the total-absorbance, the method further comprises the step of:
inputting said set of weighting factors.

4. The COD measuring method according to claim 1, wherein, within the step of detecting the absorbance of said light, said absorbance at said wavelengths of said light is simultaneously detected.

5. The COD measuring method according to claim 1, wherein the step of detecting the absorbance of said light further comprises:
measuring turbidity of said sample water.

6. The COD measuring method according to claim 1, wherein the step of detecting the absorbance of said light further comprises:
separating said light transmitted through said sample water into said wave lengths of said light.

7. The COD measuring method according to claim 1, wherein the step of detecting the absorbance of said light further comprises:
detecting light intensity at said wavelengths.

8. The COD measuring method according to claim 1, further comprising the steps of:
measuring the absorbances at the wavelengths and COD values at a plurality of periods of time with respect to a sample water to be measured;
preparing a plurality of the COD conversion equations, which indicate relationships between respective total-absorbance values obtained by subjecting the absorbance for the COD components to respective weighting processes and the measured COD values; and
among the plurality of COD conversion equations, determining the equation that exhibits the best correlation as the COD conversion equation for the sample water.

9. The COD measuring method according to claim 8, wherein, correlation coefficients are used for the determination on the superiority or inferiority of the correlation.

10. The COD measuring method according to claim 9, wherein, relative errors between the converted COD values and the measured COD values are used for the determination on the superiority or inferiority of the correlation.

11. The COD measuring method according to claim 8, wherein, relative errors between the converted COD values and the measured COD values are used for the determination on the superiority or inferiority of the correlation.

12. The COD measuring method according to claim 8, wherein the COD conversion equation is expressed by the following linear regression equation:

$y = a + bx$ where
y: the measured COD value,
x: the total-absorbance value,
$x = c_1 \cdot Ab_1 + c_2 \cdot Ab_2 + \ldots + c_m \cdot Ab_m - Vis$
$Ab_1$ to $Ab_m$: absorbance at each of wavelengths within an ultraviolet region,
$c_1$ to $c_m$: weighting factor to absorbance at each of wavelength
Vis: absorbance at wave length within a visible region,
a: intercept,
b: gradient.

13. A COD measuring device comprising:
a light source adapted to emit spectra of light;
a measuring cell, said light being transmissible through sample water contained within said measuring cell;
a detector adapted to detect an absorbance of said light transmitted through said sample water, said absorbance being detected at wavelengths within said spectra; and
a computing unit adapted to calculate a total-absorbance for said sample water, said total-absorbance being a total of weighted absorbances,
wherein each of said weighted absorbances is said absorbance at one of said wavelengths within an ultraviolet range multiplied by a weighting factor from a set of said weighting factors, and
wherein said absorbance for said wavelengths within an ultraviolet region of said spectra is uniquely associated with a weighting factor from a set of said weighting factors.

14. The COD measuring device according to claim 13, wherein said total is a sum total of weighted absorbances minus said absorbance at wavelengths within a visible region of said spectra.

15. The COD measuring device according to claim 13, wherein said set of weighting factors is input to said computing unit.

16. The COD measuring device according to claim 13, wherein said absorbance of said light transmitted through sample water is simultaneously detected.

17. The COD measuring device according to claim 13, wherein said sample water flows through said measuring cell.

18. The COD measuring device according to claim 13, wherein said spectra includes a visible region for measuring turbidity of said sample water.

19. The COD measuring device according to claim 13, wherein said detector includes a grating, said grating being adapted to separate said light transmitted through said sample water into said wavelengths of said light.

20. The COD measuring device according to claim 19, wherein an aperture is between said measuring cell and said grating.

21. The COD measuring device according to claim 13, wherein said detector includes a photoarray.

22. The COD measuring device according to claim 21, wherein said photoarray detects light intensity at said wavelengths.

23. The COD measuring device according to claim 13, wherein the computing unit further comprises:
a COD conversion equation calculation unit that calculates COD conversion equations based upon the relationship between the total-absorbance derived from absorbance values detected by the detector at a plurality of wavelengths and measured COD values on the sample water, calculating the COD conversion equations on a plurality set of weighting factors; and
a correlation calculation unit that calculates a correlation with respect to each of the COD conversion equations calculated by the COD conversion equation calculation unit,
wherein the COD conversion equation holding unit holds the conversion equation having the best correlation found by the correlation calculation unit among the COD conversion equations calculated by the COD conversion calculation unit, as the COD conversion equation for the sample water.

24. The COD measuring device according to claim 23, wherein the correlation calculation unit calculates a correlation coefficient as the correlation.

25. The COD measuring device according to claim 24, wherein the correlation calculation unit calculates a relative error between a converted COD value obtained by each of the COD conversion equations and a measured COD value as the correlation.

26. The COD measuring device according to claim 23, wherein the correlation calculation unit calculates a relative error between a converted COD value obtained by each of the COD conversion equations and a measured COD value as the correlation.

* * * * *